US008329936B2

(12) United States Patent
Friese et al.

(10) Patent No.: US 8,329,936 B2
(45) Date of Patent: Dec. 11, 2012

(54) METHOD FOR PRODUCING CYANOACRYLATE ESTERS IN THE PRESENCE OF TRANSITION METAL CATALYSTS

(75) Inventors: Carsten Friese, Duesseldorf (DE); Andreas Kirschning, Celle (DE); Ludovic Coutable, Ulm (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/342,469

(22) Filed: Jan. 3, 2012

(65) Prior Publication Data

US 2012/0203021 A1 Aug. 9, 2012

Related U.S. Application Data

(63) Continuation of application No. PCT/EP2010/059155, filed on Jun. 28, 2010.

(30) Foreign Application Priority Data

Jul. 8, 2009 (DE) .................... 10 2009 027 545

(51) Int. Cl.
C07C 253/30 (2006.01)
(52) U.S. Cl. ........................ 558/442; 558/443
(58) Field of Classification Search .................. None
See application file for complete search history.

(56) References Cited

U.S. PATENT DOCUMENTS

| 3,975,422 A | | 8/1976 | Buck |
| 5,183,930 A | | 2/1993 | Venter et al. |
| 5,502,240 A | * | 3/1996 | Pugach et al. ............. 560/99 |
| 6,245,933 B1 | * | 6/2001 | Malofsky et al. ............. 558/381 |
| 6,407,272 B1 | * | 6/2002 | Nelson et al. ............. 554/213 |
| 6,667,031 B2 | | 12/2003 | Azevedo |
| 2010/0249404 A1 | | 9/2010 | Friese et al. |
| 2012/0215023 A1 | * | 8/2012 | Friese et al. ............. 558/442 |

FOREIGN PATENT DOCUMENTS

| DE | 10111508 | 9/2002 |
| DE | 102007059967 | 6/2009 |
| EP | 0574632 | 1/1996 |
| EP | 0764148 | 3/1997 |
| JP | 2006-335663 | * 12/2006 |
| SU | 726086 | 4/1980 |
| WO | 02072535 | 9/2002 |
| WO | 03054102 | 7/2003 |

OTHER PUBLICATIONS

Blandy, Christine et al., "Homogeneous and Supported Titanates as Catalysts for Transesterification of Acrylic Esters", Catalysis Letters, 43, (1-2), 139-42, 1997.*
Machine Translation of JP 2006-335663, Dec. 14, 2006.*
International Search Report issued in connection with International Patent Application No. PCT/EP2010/059155 mailed on Sep. 2, 2010.
Ma et al., Journal of Molecular Catalysis A: Chemical 222 (2004) 183-187.
Srinivas et al., Catalysis Today 96 (2004) 127-133.
Lu et al., Angew. Chem. 2007, 119, 1242-1266.
Ceylan et al., Angew. Chem. 2008, 120, 9083-9086.

* cited by examiner

*Primary Examiner* — Fiona T Powers
(74) *Attorney, Agent, or Firm* — Steven C. Bauman

(57) ABSTRACT

The present invention relates to a method for producing cyanoacrylic acid esters. The method is based substantially on a transesterification reaction, wherein the transesterification reaction is performed in the presence of at least one transition metal catalyst that is formed by reacting at least one hydroxyl group-containing support material with at least one transition metal alkoxide.

15 Claims, No Drawings

METHOD FOR PRODUCING CYANOACRYLATE ESTERS IN THE PRESENCE OF TRANSITION METAL CATALYSTS

The present invention relates to a method for producing cyanoacrylic acid esters. The method is based substantially on a transesterification reaction, wherein the transesterification reaction is performed in the presence of at least one transition metal catalyst that is formed by reacting at least one hydroxyl group-containing support material with at least one transition metal alkoxide.

Polymerizable adhesive compositions based on cyanoacrylic acid esters are widely used in both industrial and medical applications because of their ease of use and the rapid curing and high strength of the resulting adhesive bond. It is known that monomeric forms of cyanoacrylates are extremely reactive and polymerize quickly in the presence of even minute amounts of a polymerization initiator, including the moisture contained in the air or present on surfaces. Polymerization is initiated by anions, free radicals, zwitterions or ion pairs. Once polymerization has started, the curing rate can be very fast. Polymerizable adhesive compositions based on cyanoacrylic acid ester have therefore proved to be attractive solutions for bonding plastics, rubbers, glass, metals, wood and also biological tissue, for example.

As disclosed in U.S. Pat. No. 6,667,031, the conventional synthesis of monocyanoacrylic acid esters is based on a Knoevenagel condensation, in which cyanoacetate is reacted with formaldehyde. The prepolymer that is formed is depolymerized at high temperatures of 150 to over 200° C. by thermal cracking, wherein the monomers formed are generally separated from the reaction solution by distillation. Thermal depolymerization is only successful if this process is carried out in the presence of stabilizers or mixtures of stabilizers that can prevent both a radical and an anionic repolymerization of the monomers formed under the reaction conditions described.

Stabilizers that prevent anionic repolymerization are generally, but not exclusively, Lewis acids, such as for example sulfur dioxide, nitrogen monoxide or boron trifluoride, or inorganic or organic Brøonstedt acids, such as for example sulfuric acid, phosphoric acid or organic sulfonic acids.

The high concentration of stabilizers used in the process often causes part of the stabilizer to be carried over during separation of the monomer from the reaction solution by distillation, and this can result in a high residual concentration of the stabilizer in the distilled cyanoacrylate monomer. In the case of sterically demanding cyanoacrylic acid esters in particular, this can lead to an undesirable overstabilization of the monomer, causing its polymerization rate to be reduced.

The production of bis-cyanoacrylates has also long been known, and can take place in the following manner:

Formaldehyde and bis-cyanoacetates are reacted in an analogous manner to the Knoevenagel condensation described above. This results in a crosslinked polymer that is scarcely capable of thermal depolymerization.

Bis-cyanoacrylates can also be produced in a retro-Diels-Alder reaction. As described in U.S. Pat. No. 3,975,422, for example, a monofunctional cyanoacrylate is first blocked with dienes. The blocked monofunctional cyanoacrylate is saponified to form the free acid. The ester is then produced from the corresponding acid chloride with a diol. Following exchange of the bis-cyanoacrylate for maleic anhydride, the pure bis-cyanoacrylate is finally obtained after repeated recrystallization from benzene. This production route comprises five stages and is therefore uneconomic.

An alternative possibility for producing bis-cyanoacrylates is taught in the European patent EP 0764148 B1.

The bis-cyanoacrylates are obtained by reacting 2-cyanoacrylic acid or alkyl esters thereof with diols, the reaction preferably being performed in solution in the presence of sulfonic acids as a catalyst. The bis-cyanoacrylates are then isolated by fractional crystallization.

The fact that relatively large amounts of sulfonic acids have to be used in order to achieve an effective esterification or transesterification reaction has proved to be a disadvantage of this method. Complete separation of the sulfonic acids from the product obtained is often difficult, which means that a marked reduction in the rate of polymerization of the individual monomer is observed in the case of sterically demanding bis-cyanoacrylates in particular, because said sulfonic acids act as anionic polymerization inhibitors.

In addition to the homogeneously catalyzed methods described, transesterification methods that proceed in the presence of heterogeneous catalysts are also known in the prior art.

X. Ma, S. Wang, J. Gong, X. Yang and G. Xu (Journal of Molecular Catalysis A: Chemical 222 (2004) 183-187) describe for example the production of $TiO_2$—, $TiO_2/SiO_2$—, $TiO_2/Al_2O_3$— and $TiO_2/MgO$-based catalysts and their successful use as heterogeneous catalyst systems in transesterification reactions of dimethyl oxalate.

D. Srinivas, R. Srivastava and P. Ratnasamy (Catalysis Today 96 (2004) 127-133) describe the production of similar catalyst systems and their successful use as heterogeneous catalyst systems in transesterification reactions of ethyl acetonate, dimethyl malonate and cyclic propylene carbonates.

EP 0574632 B1 teaches a method for producing carboxylic acid esters using a catalyst obtained by reacting prepared transition metal oligomers with a solid substrate having hydroxyl groups at its surface.

None of the cited documents discloses the use of heterogeneous catalysts in transesterification reactions of cyanoacrylic acid esters.

The object of the present invention was to develop an alternative method for producing cyanoacrylic acid esters that allows said esters to be produced in a high purity with as low as possible a residual concentration of anionic polymerization inhibitors.

The solution according to the invention can be ascertained from the claims. It consists substantially of the transesterification of cyanoacrylic acid esters with monohydric and/or polyhydric alcohols in the presence of at least one transition metal catalyst that is formed by reacting at least one hydroxyl group-containing support material with at least one transition metal alkoxide.

The at least one transition metal catalyst enables the transesterification reaction of the method according to the invention to be performed with high yields even without the addition of Brønstedt acids, resulting in transesterification products of high purity and high reactivity having an extremely low residual concentration of anionic polymerization inhibitors.

The present invention therefore provides a method for producing at least one cyanoacrylic acid ester of the general formula (I),

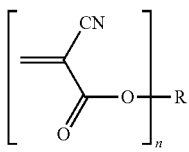

Formula (I)

comprising the following steps:
a) transesterification of at least one 2-cyanoacrylic acid ester of the general formula (II),

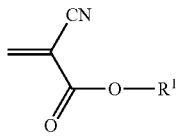

Formula (II)

in which $R^1$ is a branched or unbranched alkyl residue having 1 to 6 C atoms, with at least one alcohol of the general formula (III),

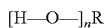            Formula (III)

in the presence of at least one transition metal catalyst that is formed by reacting at least one hydroxyl group-containing support material with at least one transition metal alkoxide, and
b) isolation of the cyanoacrylic acid ester of the general formula (I) obtained in step a), n being a whole number from 1 to 6 and R being an n-valent residue comprising 1 to 100 C atoms.

As the method according to the invention is a transesterification reaction, the residues R and $R^1$ can be non-identical. In particular it is preferable for residue R to have at least one C atom, in particular at least two C atoms more than residue $R^1$.

All compounds that are formed by reacting at least one hydroxyl group-containing support material with at least one transition metal alkoxide and having a catalytic activity in the transesterification reaction performed in the method according to the invention are suitable as the transition metal catalyst within the meaning of the present invention.

Within the meaning of the invention the term "transition metal" denotes a metallic element chosen from groups Ib, IIb, IIIa (including the lanthanoids), IVa, Va, VIa, VIIa and VIII of the periodic table, published in the supplement to the Bulletin de la Société Chimique de France no. 1 (January 1966). In other words it is an element whose atomic number is between 21 and 30 inclusive, between 39 and 48 inclusive or between 57 and 80 inclusive.

Within the meaning of the present invention an n-valent residue R is understood to be an n-valent organic radical having 1 to 100 C atoms that is formally formed starting from the cyanoacrylic acid ester of the general formula (I) or the alcohol of the general formula (III) by the homolytic cleavage of n carbon-oxygen bonds.

The concept of the n-valent residue is described in more detail below by reference by way of example to the example of the trihydric alcohol trimethylolpropane (TMP; n=3):

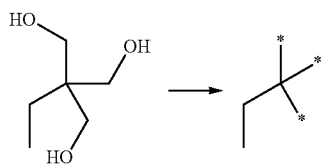

Within the meaning of the present invention the formal homolytic cleavage of the three C—OH bonds in the TMP molecule results in a trivalent organic residue.

Both monocyanoacrylic acid esters and higher cyanoacrylic acid esters can be produced by the method according to the invention, depending on the alcohol used.

In a preferred embodiment of the method according to the invention the cyanoacrylic acid ester of the general formula (I) is therefore selected from monocyanoacrylic acid esters of the general formula (Ia),

Formula (Ia)

and/or from bis-cyanoacrylic acid esters of the general formula (Ib),

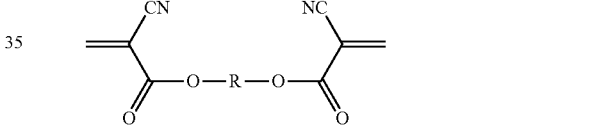

Formula (Ib)

and/or from tris-cyanoacrylic acid esters of the general formula (Ic),

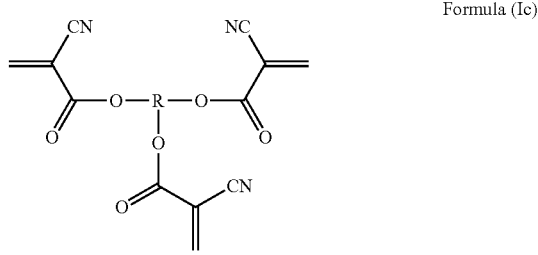

Formula (Ic)

the residues R being defined as above.

The method according to the invention is suitable in particular for producing bis-cyanoacrylic acid esters of the general formula (Ib) and/or tris-cyanoacrylic acid esters of the general formula (Ic). Owing to the high reactivity of the transition metal catalyst used, the aforementioned cyanoacrylic acid esters can be prepared in very high purities. At the same time the cited molecules have a very high reactivity in the corresponding polymerization reactions, as the use of Brønstedt acids as transesterification catalysts is entirely or almost entirely dispensed with in the transesterification method according to the invention.

In a preferred embodiment of the method according to the invention the residue R in formula (I), formula (Ia), formula (Ib), formula (Ic) and/or formula (III) comprises a $C_3$ to $C_{100}$ chain, preferably a $C_5$ to $C_{70}$ chain and in particular a $C_{10}$ to $C_{50}$ chain, that is interrupted by at least one oxygen atom. The residue R can have a linear, branched or cyclic configuration.

Residues R are preferred in particular that have at least one polyethylene glycol and/or at least one polypropylene glycol unit.

In a preferred embodiment of the method according to the invention the residue R in formula (I), formula (Ia), formula (Ib), formula (Ic) and/or formula (III) comprises 3 to 18, in particular 4, 8, 10 and/or 12 directly linked C atoms. The residue R can likewise have a linear, branched or cyclic configuration.

The residue R can moreover contain an aromatic group or in addition to hydrogen and carbon atoms can also encompass at least one heteroatom, selected for example from halogen, oxygen and/or nitrogen atoms.

The alcohols of the general formula (III)

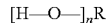  Formula (III)

are monohydric to hexahydric alcohols (n=1 to 6), mono-, di- and/or trihydric alcohols being preferred. The monocyanoacrylic acid esters of the general formula (Ia), the bis-cyanoacrylic acid esters of the general formula (Ib) and the tris-cyanoacrylic acid esters of the general formula (Ic) depicted above can be readily prepared with the aid of these alcohols.

The alcohols used in the method according to the invention are preferably primary or secondary alcohols, primary alcohols being preferred because they have a higher reactivity in the transesterification reaction. Any mixtures of different alcohols can generally also be used.

Suitable alcohols can be selected for example from ethanol, chloroethanol, cyanoethanol, n-propanol, sec-propanol, n-butanol, tert-butanol, isoamyl alcohol, n-hexanol, 2-ethylhexanol, n-octanol, n-decanol, isodecanol, cyclohexanol, benzyl alcohol, ortho-, meta- and para-methoxybenzyl alcohol, ethylene glycol, 1,2-propylene glycol, 1,3-propylene glycol, 1,2-butanediol, 1,3-butanediol, 1,4-butanediol, 1,4-pentanediol, 3-methyl-1,5-pentanediol, 2,3-dimethyl-2,3-butanediol, phenylethyl alcohol, triphenylethyl alcohol, trimethylolpropane, mannitol, sorbitol, glycerol, pentaerythritol, 1,4-cyclohexane dimethanol, xylenol, bisphenols, diethylene glycol, triethylene glycol, polyoxyethylene or polyoxypropylene glycols preferably having a molecular weight of up to approximately 4000, diethylene glycol monomethyl ether, diethylene glycol monoethyl ether, triethylene glycol monomethyl ether, butoxyethanol, butylene glycol monobutyl ether, dipentaerythritol, tetrapentaerythritol, diglycerol, triglycerol and the like.

In a preferred embodiment of the present invention the alcohol of the general formula (III) used in the method according to the invention is also selected from compounds of the general formula (IIIa)

  Formula (IIIa)

in which $R^2CO$ denotes a linear or branched acyl residue having 12 to 22 carbon atoms and m denotes numbers from 5 to 30 and preferably from 15 to 25. Typical examples are addition products of ethylene oxide with lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof, which form for example in the pressurized cleavage of natural fats and oils or in the reduction of aldehydes from the Roelen oxo synthesis. Addition products of ethylene oxide with fatty acids having 16 to 18 carbon atoms are preferably used.

According to the method according to the invention the alcohols of the formula (III) are reacted with at least one 2-cyanoacrylic acid ester of the general formula (II)

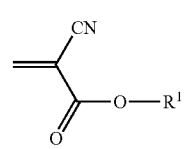  Formula (II)

in which $R^1$ is a branched or unbranched alkyl residue having 1 to 6 C atoms.

Within the meaning of the present invention methyl-2-cyanoacrylate or ethyl-2-cyanoacrylate are preferred 2-cyanoacrylic acid esters, as the alcohol methanol or ethanol that is formed in the transesterification reaction can easily be removed. Mixtures of different 2-cyanoacrylic acid esters can likewise be used, mixtures of methyl-2-cyanoacrylate or ethyl-2-cyanoacrylate being preferred.

The at least one 2-cyanoacrylic acid ester of the general formula (II) is preferably used in excess in the method according to the invention. The molar ratio of 2-cyanoacrylic acid ester to the alcohol of the general formula (III) ranges from 20:1 to 1:1, preferably from 10:1 to 1.5:1.

The transesterification (step a) of the method according to the invention is performed in the presence of at least one transition metal catalyst, the cited transition metal catalyst being formed by reacting at least one hydroxyl group-containing support material with at least one transition metal alkoxide that is preferably selected from transition metal alkoxides of the general formula (IV),

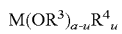  Formula (IV)

in which a denotes 3, 4 or 5, u is either 0, 1 or 2, M denotes a transition metal, $R^3$ is a linear or branched optionally substituted C1-20 alkyl group or an optionally substituted C6-12 aryl group and $R^4$ denotes a linear or branched optionally substituted C1-4 alkyl group.

The transition metal catalyst used in the method according to the invention preferably has the characterizing feature that it is substantially insoluble in the reaction mixture.

The term "reaction mixture" is understood to be a mixture comprising at least one cyanoacrylic acid ester of the general formula (I) and at least one alcohol of the general formula (III) and optionally further solvents, such as for example organic solvents.

Within the meaning of the invention the term "substantially insoluble" is preferably understood to mean that under the chosen reaction conditions less than 20 mol %, preferably less than 10 mol %, particularly preferably less than 5 mol % and in particular less than 1 mol % of all transition metal atoms of the originally used transition metal catalyst can be detected in the reaction mixture. Detection can take place for example by atomic emission spectroscopy (AES).

The transesterification reaction of the present invention is a heterogeneously catalyzed method. Such a method is advantageous as the transition metal catalyst can be easily separated from the reaction mixture and the product of the method has only an extremely low residual concentration of said catalyst.

In a special embodiment at least one transition metal in the transition metal catalyst and in particular the transition metal M in formula (IV) is selected from titanium, zirconium, hafnium, iron, zinc or vanadium, titanium being particularly preferred.

The aforementioned alkyl and/or aryl groups can bear one or more halogen atoms and/or heteroatoms as substituents, the heteroatoms being a component of a functional group that is selected for example from primary and secondary amines, amides, urethanes, alcohols, ethers, esters, thiols, thioethers and sulfones.

Methoxy, ethoxy, n-propoxy, isopropoxy, n-butoxy, isobutoxy, tert-butoxy, 2-ethylhexyloxy, n-decyloxy, tridecyloxy and phenoxy groups are preferred in particular as the alkoxy group $OR^2$ having 1 to 20 C atoms, wherein in particular alkyl groups having 1 to 4 C atoms, preferably having 2, 3 or 4 C atoms, can be used as the alkoxy group $OR^2$.

If u has the value 1, $R^3$ is preferably selected from methyl, ethyl, propyl and isopropyl groups.

The transition metal alkoxide of the present invention is in particular a titanium tetraalkoxide, such as for instance tetra-n-butyl titanate, tetra-t-butyl titanate, tetra-n-propyl titanate, tetra-isopropyl titanate, tetraphenyl titanate, tetracyclohexyl titanate and tetrabenzyl titanate or a trialkoxy monoalkyl titanium compound.

Before and/or during the reaction with the hydroxyl group-containing support material the transition metal alkoxide of the general formula (IV) can furthermore be converted into a transition metal oligomer by partial hydrolysis.

Within the meaning of the present invention a transition metal oligomer is understood in particular to be a compound comprising 10 to 10,000 transition metal atoms, the individual transition metal atoms being coupled together by bridging oxygen atoms.

The amount of water can vary within a broad range, depending on the extent of the desired degree of oligomerization. One mol of water is necessary for every mol of oxygen bridge that is formed. Both straight-chain and branched oligomers are formed during the partial hydrolysis. The partial hydrolysis can be performed in any organic solvent in which the transition metal alkoxide is soluble and stable. However, it is typically performed in the alcohol corresponding to that of the transition metal alkoxide. The water can equally be pure or diluted. It is often diluted with the solvent used to dissolve the transition metal alkoxide. The water or water solution is usually added dropwise, the temperature, pressure and rate of addition being adjusted to the reactivity of the individual transition metal alkoxide. After the reaction the solvent does not necessarily have to be removed. For the reaction with the hydroxyl group-containing support material it can be convenient to remove the solvent and replace it with a different solvent.

In an alternative embodiment the reaction of the transition metal alkoxide, in particular the transition metal alkoxide of the general formula (IV), with the hydroxyl group-containing support material takes place under anhydrous conditions. In this way the tendency to oligomerization is minimized, causing other transition metal catalysts with different reactivities to be obtained.

In its structure and its chemical composition the hydroxyl group-containing support material is subject to no special limitations within the meaning of the present invention, provided that it allows binding (immobilization), in particular covalent binding of at least one suitable transition metal alkoxide.

Examples having a large number of hydroxyl groups on the surface are conventionally used as hydroxyl group-containing supports materials.

The hydroxyl group-containing support material can be either natural or synthetic. Examples are carbohydrate-based polymers, cyclodextrins, aluminum oxide, silicon dioxide, quartz dust, silica gel, clays (such as e.g. kaolinite, montmorillonite, vermiculite, chlorite and mica types), zeolites, zirconium oxide, titanium oxide, thorium oxide, magnesium oxide, aluminates, carbon black, synthetic inorganic oxides of silicon, magnesium, aluminum, zinc, and mixtures thereof and the like.

The hydroxyl group-containing support material is preferably selected from silicon dioxide, aluminum oxide and mixtures thereof. In addition, organic polymers having hydroxyl groups can also be used. Oxides of silicon and aluminum are preferred hydroxyl group-containing supports materials.

Suitable methods for producing the transition metal catalysts of the present invention can be taken for example from the aforementioned publications by X. Ma, S. Wang, J. Gong, X. Yang and G. Xu (Journal of Molecular Catalysis A: Chemical 222 (2004) 183-187) and D. Srinivas, R. Srivastava and P. Ratnasamy (Catalysis Today 96 (2004) 127-133).

In a special embodiment the transition metal catalyst of the present invention is calcined before use in the method according to the invention, in other words it is exposed to an elevated temperature over a certain period of time in the presence of oxygen.

Suitable transition metal catalysts can therefore also be obtained by reacting at least one hydroxyl group-containing support material with at least one transition metal alkoxide, the reaction product then being exposed to temperatures of 150° C. to 800° C. in the presence of oxygen. Preferred temperatures are between 300° C. and 700° C., in particular between 400° C. and 600° C.

Suitable oxygen sources are in particular mixtures of various gases, wherein the oxygen content should be at least 10 wt. %. The calcination can be performed in particular in the presence of air.

The chemical structure of the transition metal catalyst is modified decisively by the calcination, resulting in many cases in an increase in the catalytic activity or allowing the catalytic activity to be adjusted to the specific requirements of a particular transesterification reaction.

Naturally any mixtures of various transition metal catalysts can be used within the context of the present invention.

Depending on the reactivity of the individual reactants and the chosen reaction conditions, the at least one transition metal catalyst is preferably used in amounts from 0.01 to 10 wt. %, particularly preferably from 0.1 to 5 wt. % and in particular from 1 to 3 wt. %, relative in each case to the total amount of the 2-cyanoacrylic acid ester of the general formula (II).

The method according to the invention is preferably performed in the presence of at least one radical polymerization inhibitor. The radical polymerization inhibitor prevents a premature polymerization of the cyanoacrylic acid esters that are used. The necessary amount can easily be determined by a person skilled in the art. Suitable radical polymerization inhibitors are for example phenol compounds, such as for instance hydroquinone, hydroquinone monomethyl ether, butylated hydroxyanisole (BHA), 2,6-di-tert-butyl-4-methylphenol (BHT), t-butylcatechol, pyrocatechin and p-methoxyphenol. Mixtures of the cited radical polymerization inhibitors can likewise be used. A particularly preferred radical polymerization inhibitor within the meaning of the present invention is butylated hydroxyanisole (BHA) and/or hydroquinone monomethyl ether.

Furthermore the method according to the invention is preferably performed in the presence of an acid that is gaseous at 22° C., in particular a Lewis acid, the acid being selected for example from sulfur dioxide and/or boron trifluoride. The cited acids stabilize the cyanoacrylic acid esters.

The transesterification reaction of the present invention can be performed under normal pressure but also under reduced pressure or excess pressure of 0.001 to 200 bar. The alcohol that is cleaved off during the transesterification is preferably distilled off continuously or after the end of the reaction, wherein the reaction can be performed in a suitable solvent such as for instance toluene, xylene or toluene/xylene mixtures. The method according to the invention is preferably performed with the aid of a distillation assembly with a high separation efficiency.

In a special embodiment the transesterification reaction (step a of the method according to the invention) is performed by heating the reaction mixture in a reactor in the presence of at least one transition metal catalyst of the present invention, the reaction mixture comprising at least one cyanoacrylic acid ester of the general formula (II) and at least one alcohol of the general formula (III) as reactants and being in contact with a solid heating medium that is capable of being heated by electromagnetic induction and that is located inside the reactor and is heated by electromagnetic induction with the aid of an inductor.

It is advantageous for the heat energy for performing the transesterification reaction not to be introduced into the reaction mixture via surfaces such as for example the reactor walls, heating coils, heat exchanger plates or similar but rather to be generated directly in the body of the reactor. The ratio of heated surface area to volume of the reaction mixture can be substantially greater than in the case of heating via heat-transferring surfaces. In addition, the efficiency of electrical current to heating capacity is improved. By switching on the inductor, heat can be generated in the entire solid heating medium, which is contact with the reaction mixture via a very large surface area. When the inductor is switched off, the further introduction of heat is very quickly stopped. This allows a very targeted reaction control and minimizes the thermal loading of the transition metal catalyst of the present invention that is involved in the reaction. Thermally unstable transition metal catalysts in particular retain their catalytic activity over a longer period of time in this way, allowing comparatively greater reaction yields to be achieved in the transesterification reaction of the present invention.

The heating medium consists of an electrically conductive material that heats up under the influence of an electromagnetic alternating field. It is preferably selected from materials having a very large surface area in comparison to their volume. For example, the heating medium can be selected from electrically conductive chips, wires, meshes, wool, membranes, porous frits, fillers such as for example granules, Raschig rings and in particular from particles, which preferably have an average diameter of no more than 1 mm. In order to be capable of being heated by electromagnetic induction, the heating medium is electrically conductive, for example metallic (wherein it can be diamagnetic), or it has an increased interaction with a magnetic field in comparison to diamagnetism and is in particular ferromagnetic, ferrimagnetic, paramagnetic or superparamagnetic. It makes no difference whether the heating medium is organic or inorganic in nature or whether it contains both inorganic and organic components.

In a preferred embodiment the heating medium is selected from particles of electrically conductive and/or magnetizable solids, wherein the particles have an average particle size in the range from 1 to 1000, in particular from 10 to 500 nm. The average particle size and if necessary also the particle size distribution can be determined by light scattering, for example. Magnetic particles, for example ferromagnetic or superparamagnetic particles, are preferably chosen that have as low as possible a remanence or residual magnetization. This has the advantage that the particles do not adhere to one another. The magnetic particles can be present for example in the form of "ferrofluids", in other words liquids in which ferromagnetic particles are dispersed in the nano-size scale. The liquid phase of the ferrofluid can then serve as the reaction mixture.

Magnetizable particles, in particular ferromagnetic particles, having the desired properties are known in the prior art and are commercially available. The commercially available ferrofluids are mentioned by way of example. Examples of the production of magnetic nanoparticles that can be used in the context of the method according to the invention can be taken from the article by Lu, Salabas and Schüth: "Magnetische nano-Partikel: Synthese, Stabilisierung, Funktionalisierung and Anwendung", Angew. Chem. 2007, 119, pages 1242 to 1266.

Suitable magnetic nanoparticles are known with differing compositions and phases. Examples that can be cited include: pure metals such as Fe, Co and Ni, oxides such as $Fe_3O_4$ and $gamma-Fe_2O_3$, spinel-like ferromagnets such as $MgFe_2O_4$, $MnFe_2O_4$ and $CoFe_2O_4$ and alloys such as $CoPt_3$ and FePt. The magnetic nanoparticles can have a homogeneous structure or a core-shell structure. In the latter case the core and shell can consist of different ferromagnetic or antiferromagnetic materials. Embodiments are also possible, however, in which a magnetizable core, which can be ferromagnetic, antiferromagnetic, paramagnetic or superparamagnetic for example, is surrounded by a non-magnetic material. This material can be an organic polymer, for example. A coating of this type can prevent a chemical interaction between the reaction mixture and the material of the magnetic particles themselves. Furthermore, the shell material can be surface-functionalized without the material of the magnetizable core interacting with the functionalizing species.

Nanoscale particles of superparamagnetic substances selected from aluminum, cobalt, iron, nickel or alloys thereof, metal oxides of the n-maghemite type ($gamma-Fe_2O_3$), n-magnetite ($Fe_3O_4$) or ferrites of the $MeFe_2O_4$ type, where Me is a divalent metal selected from manganese, copper, zinc, cobalt, nickel, magnesium, calcium or cadmium, can be used for example as the heating medium. These particles preferably have an average particle size of $\leq 100$ nm, preferably $\leq 51$ nm and in particularly preferably $\leq 30$ nm.

Nanoscale ferrites such as are known for example from WO 03/054102 can be used as the heating medium. These ferrites have a $(M^a_{1-x-y}M^b_xFe^{II}_y) Fe^{III}_2O_4$ composition, in which $M^a$ is selected from Mn, Co, Ni, Mg, Ca, Cu, Zn, Y and V,
$M^b$ is selected from Zn and Cd,
x denotes 0.05 to 0.95, preferably 0.01 to 0.8,
y denotes 0 to 0.95 and
the sum of x and y is at most 1.

The particles that are capable of being heated by electromagnetic induction can constitute the heating medium with no further additives. However, it is also possible to mix the particles that are capable of being heated by electromagnetic induction with other particles that are not capable of being heated by electromagnetic induction. Sand is one example. The inductively heatable particles can therefore be diluted by non-inductively heatable particles. An improved temperature control can be achieved in this way.

If nanoscale particles capable of being heated by electromagnetic induction are mixed with coarser, non-inductively heatable particles, this can lead to a reduction in the packing density of the heating medium. In embodiments in which the reaction medium flows through a packing consisting of the heating medium, this can result in a desired reduction in the pressure loss in the reactor through which the medium flows.

The surface of the solid heating medium can be coated with a catalytically active substance. For example a transition metal alkoxide of the general formula (IV) can be immobilized on the surface of the heating medium, which likewise results in a transition metal catalyst within the meaning of the present invention.

In a special embodiment of the invention the surface of the heating medium thus bears a hydroxyl group-containing layer, which can be used to bind transition metal alkoxides of the general formula (IV). Alternatively, before and/or during binding to the hydroxyl group-containing layer, the transition metal alkoxides of the general formula (IV) can be converted into a transition metal oligomer by partial hydrolysis, the term "transition metal oligomer" being defined as above.

Nanoscale particles having at their surface an $SiO_2$ layer as the hydroxyl group-containing layer, which can be used for covalent binding of the non-hydrolyzed or partially hydrolyzed transition metal alkoxides, are preferred in particular as the heating medium.

The transesterification reaction (step a of the present method) can in principle be performed continuously or batchwise. If the reaction is performed batchwise, the reaction mixture and the inductively heated solid heating medium are preferably moved relative to each other during the reaction. If a particulate heating medium is used, this can take place in particular by stirring the reaction mixture together with the heating medium or by vortexing the heating medium in the reaction mixture. If for example meshes or wool of a thread-like heating medium are used, the reaction vessel containing the reaction mixture and the heating medium can be shaken for example.

A preferred embodiment of a transesterification reaction performed batchwise consists of placing the reaction mixture in a reaction vessel together with particles of the heating medium and moving it with the aid of a moving element located in the reaction mixture, the moving element being set up as an inductor by means of which the particles of the heating medium are heated by electromagnetic induction. Thus in this embodiment the inductor is located inside the reaction mixture. The moving element can take the form of a stirrer or a vertically moving plunger, for example.

It can additionally be provided that the reactor is externally cooled during the chemical reaction. This is possible in batch operation in particular, if, as stated above, the inductor is immersed in the reaction mixture. The introduction of the electromagnetic alternating field into the reactor is then not inhibited by the cooling device.

The reactor can be cooled internally via cooling coils or heat exchangers or preferably externally. Optionally pre-cooled water or a cooling mixture whose temperature is below 0° C. can be used for cooling, for example. Examples of such cooling mixtures are ice/common salt mixtures, methanol/dry ice or liquid nitrogen. Cooling allows a temperature gradient to be established between the reactor wall and the inductively heated heating medium. This is particularly pronounced if a cooling mixture with a temperature well below 0° C. is used, for example methanol/dry ice or liquid nitrogen. The reaction mixture that is heated by the inductively heated heating medium is then cooled again externally. The transesterification reaction of the present invention thus preferably takes place only if the reactants are in contact with the heating medium or are at least in its immediate vicinity. Owing to the movement of the reaction mixture relative to the heating medium, the cyanoacrylic acid ester of the general formula (I) that is formed in the reaction quickly moves into the cooler areas of the reaction mixture, thus inhibiting its further thermal reaction.

In an alternative embodiment the transesterification reaction of the present invention is performed continuously in a continuous-flow reactor that is at least partially filled with the solid heating medium and thus has at least one heating zone that is capable of being heated by electromagnetic induction, the reaction mixture flowing continuously through the continuous-flow reactor and the inductor being located outside the reactor. The continuous-flow reactor is preferably designed as a tubular-flow reactor. In this case the inductor can surround the reactor completely or at least partially. The electromagnetic alternating field generated by the inductor is then introduced on all sides or at least from several points into the reactor.

In this continuous processing mode in a continuous-flow reactor it is possible for the reactor to have several heating zones. For example, different heating zones can be heated to differing extents. This can be achieved either by the positioning of different heating media in the continuous-flow reactor or by means of differently configured inductors along the reactor.

It can also be provided that after leaving the heating zone the reaction mixture is brought into contact with an absorber substance that removes by-products or impurities from the reaction mixture.

Depending on the reactivity of the transition metal catalyst and the reactants used, the product yield can optionally be increased by returning at least part of the reaction mixture that has flowed through the solid heating medium to flow through the solid heating medium again. It can be provided for impurities, by-products or the desired main product to be removed from the reaction mixture after each passage through the solid heating medium. The various known separating methods are suitable for this purpose, for example absorption on an absorber substance, precipitation by cooling or separation by distillation. A complete reaction of the reactants can ultimately be achieved in this way.

The overall contact time of the reaction mixture with the inductively heated heating medium that is conveniently chosen is dependent on the kinetics of the transesterification reaction of the present invention. The slower the transesterification reaction, the longer the chosen contact time should be. This must be adjusted empirically in the individual case. As a reference point, the reaction mixture should preferably pass through the tubular-flow reactor one or more times at a rate such that the overall contact time of the reaction mixture with the inductively heated heating medium is in the range from approximately 1 second to approximately 2 hours. Shorter contact times are conceivable, but are more difficult to control. Longer contact times can be necessary with particularly slow transesterification reactions of the present invention, but they incrementally reduce the cost-effectiveness of the method.

Regardless of whether the transesterification reaction of the present invention is performed batchwise or continuously in a continuous-flow reactor, it can be provided for the reactor to be designed as a pressure reactor and for the transesterification reaction to be performed at a pressure above 1013 mbar, preferably at least 1.5 bar.

In a special embodiment of the method according to the invention the heating medium is ferromagnetic and has a Curie point in the range from approximately 40 to approximately 250° C., which is selected such that the Curie point differs by no more than 20° C., preferably by no more than 10° C., from the selected reaction temperature. This leads to an inherent protection against inadvertent overheating. The heating medium can only be heated by electromagnetic induction up to its Curie point, while at a higher temperature it is no longer heated by the electromagnetic alternating field. Even if the inductor malfunctions, the temperature of the reaction mixture can be prevented in this way from rising inadvertently to a value well above the Curie point of the heating medium. If the temperature of the heating medium falls below its Curie point again, it can once again be heated by electromagnetic induction. This leads to a self-regulation of the temperature of the heating medium in the vicinity of the Curie point and allows even thermally unstable transesterification catalysts to be used with a high degree of process safety, provided their decomposition temperature is below the Curie point of the heating medium.

It goes without saying that the nature of the heating medium and the design of the inductor must be matched to one another so that the reaction mixture can be heated in the desired way. Critical variables here are the output of the inductor expressed in Watts and the frequency of the alternating field generated by the inductor. In principle, the greater the mass of the heating medium to be heated inductively, the higher the chosen output must be. In practice, the achievable output is limited in particular by the possibility of cooling the generator needed to supply the inductor.

Inductors generating an alternating field with a frequency in the range from approximately 1 to approximately 100 kHz, in particular in the range from approximately 10 to approximately 30 kHz, are particularly suitable. Such inductors and the associated generators are available commercially, for example from IFF GmbH in Ismaning, Germany.

On completion of the transesterification reaction (step a) it is advantageous to separate the transition metal catalyst from the reaction mixture. Separation can take place by any method familiar to the person skilled in the art, separation by filtration and/or by centrifugation being preferred in particular.

By virtue of the ready separability of the transition metal catalyst, the cyanoacrylic acid ester of the general formula (I) obtained in the method according to the invention can be isolated in a highly pure form, in particular by distillation or crystallization, with product purities of greater than 98% being achievable.

The cyanoacrylic acid esters produced in this way can be used for bonding components, in particular for bonding electrical and/or electronic components, and for producing medical adhesives for treating surgically cut or traumatically torn tissue.

The present invention is illustrated in further detail by the following examples, without being limited thereto.

EMBODIMENT EXAMPLES

Substances Used

Tetraisopropyl titanate and methyl lithium were ordered from Sigma Aldrich and used with no further purification. 1-Decanol was ordered from Merck and used with no further purification. Titanium tetrachloride was distilled over copper before use. Silica gel (silica 60, 0.04-0.063 mm, 230-400 mesh, specific surface area 500 m$^2$/g) was ordered from Macherey-Nagel. Methyl-2-cyanoacrylate [CAS 137-05-3] is commercially available and can be purified before use in the method according to the invention by distillation.

1. Production of Methyl Triisopropyl Titanate.

In a 100 ml Schlenk flask TiCl$_4$ (1.10 ml, 10.0 mmol) was added slowly to Ti(Oi-Pr)$_4$ (8.98 ml, 30.0 mmol) in dry diethyl ether (5 ml) at 0° C. and the resulting mixture was stirred for 10 min at 0° C. After stirring for 30 minutes at 22° C. dry diethyl ether (15 ml) was added and the mixture cooled to −40° C. Then a solution of MeLi (1.6 M in Et$_2$O, 25.0 ml, 40.0 mmol) was added dropwise. The yellow mixture that was obtained was stirred for 10 min at −40° C. and then heated to 0° C. within 45 min. Methyl triisopropyl titanate (MeTi(Oi-Pr)$_3$) was able to be isolated by distillation under reduced pressure.

2. Production of the Metal Catalyst 1

A suspension of silica gel (6.00 g, predried under vacuum at 150° C. for 20 h) in anhydrous toluene (30 ml) was mixed with a suspension of MeTi(Oi-Pr)$_3$ (1.44 g, 6.00 mmol) in anhydrous toluene (80 ml). The resulting reaction mixture was shaken for 16 h at 22° C. The metal catalyst 1 that was obtained was then separated off by filtration, washed with toluene and dried under vacuum for 24 h.

3. Transesterification Reaction

A reaction setup by way of example can be taken from the following publication: Angew. Chem. 2008, 120, 9083-9086.

General Experimental Procedure

A glass reactor (length 14 cm×internal diameter 9 mm) was filled with steel balls and the metal catalyst 1 (1.8 g). After rinsing the reactor with anhydrous toluene (10 ml, flow rate: 0.5 ml/min), a solution of methyl-2-cyanoacrylate (MCA) (1.01 ml, 10.0 mmol, 10 eq.), 1-decanol (0.19 ml, 1.00 mmol, 1 eq.) and hydroquinone (0.005 eq./MCA) and trifluoromethanesulfonic acid (0.001 eq./MCA) in anhydrous toluene (10 ml) was pumped through the reactor (flow rate 0.1-1.0 ml/min), wherein the reactor was heated to approx. 90° C. by means of an inductive heating device (field frequency 20 kHz, 310 per mil). Then the reactor was rinsed with anhydrous toluene (5 ml at 0.2 ml/min, then 10 ml at 0.4 ml/min) and the solution obtained was concentrated under vacuum. The reactor output was analyzed by means of NMR spectrometry methods.

Decyl-2-cyanoacrylate was able to be isolated in good yields by the method according to the invention, wherein the product obtained contained only a small proportion of by-products.

What is claimed:

1. A method for producing at least one cyanoacrylic acid ester of the formula (I),

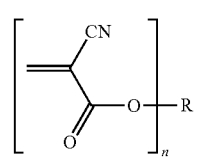

Formula (I)

comprising the following steps:
a) transesterification of at least one 2-cyanoacrylic acid ester of the formula (II),

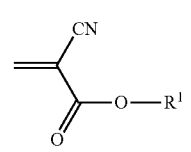

Formula (II)

in which R¹ is a branched or unbranched alkyl residue having 1 to 6 C atoms, with at least one alcohol of the general formula (III),

[H—O—]$_n$R  Formula (III)

in the presence of at least one transition metal catalyst that is formed by reacting at least one hydroxyl group-containing support material with at least one transition metal alkoxide, and b) isolation of the cyanoacrylic acid ester of the formula (I) obtained in step a), n being a whole number from 1 to 6 and R being an n-valent residue comprising 1 to 100 C atoms.

2. The method according to claim 1, wherein the cyanoacrylic acid ester of the formula (I) is selected from monocyanoacrylic acid esters of the formula (Ia),

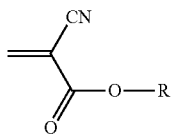

Formula (Ia)

and/or from bis-cyanoacrylic acid esters of the formula (Ib),

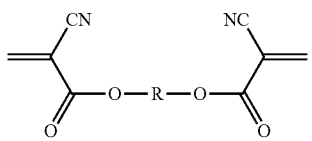

Formula (Ib)

and/or from tris-cyanoacrylic acid esters of the formula (Ic),

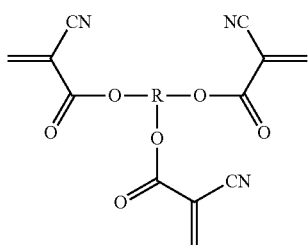

Formula (Ic)

the residue R comprising 1 to 100 C atoms.

3. The method according to claim 1, wherein the residue R in formula (I), formula (Ia), formula (Ib), formula (Ic) and/or formula (III) comprises a $C_3$ to $C_{100}$ chain that is interrupted by at least one oxygen atom.

4. The method according to claim 1, wherein the residue R in formula (I), formula (Ia), formula (Ib), formula (Ic) and/or formula (III) comprises 3 to 18 directly linked C atoms.

5. The method according to claim 1, wherein the 2-cyanoacrylic acid ester of the formula (II) is selected from methyl-2-cyanoacrylate and ethyl-2-cyanoacrylate.

6. The method according to claim 1, wherein the hydroxyl group-containing support material is selected from aluminum oxide, silicon dioxide, quartz dust, silica gel, clays, zeolites, zirconium oxide, titanium oxide, thorium oxide or magnesium oxide.

7. The method according to claim 1, wherein the transition metal alkoxide is selected from compounds of the formula (IV), $M(OR^3)_{a-u}R^4_u$  Formula (IV)

in which a denotes 3, 4 or 5, u is either 0, 1 or 2, M denotes a transition metal, $R^3$ is a linear or branched optionally substituted C1-20 alkyl group or an optionally substituted C6-12 aryl group and $R^4$ denotes a linear or branched optionally substituted C1-4 alkyl group.

8. The method according to claim 1, wherein at least one transition metal in the transition metal alkoxide is selected from titanium, zirconium, hafnium, iron, zinc or vanadium.

9. The method according to claim 1, wherein the transition metal alkoxide is selected from titanium alkoxides.

10. The method according to claim 1, wherein the transition metal catalyst is obtained by reacting at least one hydroxyl group-containing support material with at least one transition metal alkoxide, the reaction product then being exposed to temperatures of 150° C. to 800° C. in the presence of oxygen.

11. The method according to claim 1, wherein the at least one transition metal catalyst is present in an amount from 0.01 to 10 wt. %, relative to the total amount of the 2-cyanoacrylic acid ester of the formula (II).

12. The method according to claim 1, wherein the method is performed in the presence of at least one radical polymerization inhibitor and/or at least one gaseous acid.

13. The method according to claim 1, wherein the transesterification reaction (step a) is performed by heating a reaction mixture in a reactor in the presence of at least one transition metal catalyst according to claim 1, the reaction mixture comprising at least one cyanoacrylic acid ester of the formula (II) and at least one alcohol of the formula (III) and being in contact with a solid heating medium that is capable of being heated by electromagnetic induction and that is located inside the reactor and is heated by electromagnetic induction with the aid of an inductor.

14. The method according to claim 13, wherein the heating medium is selected from chips, wires, meshes, wool, membranes, frits, fillers and particles, preferably selected from particles of electrically conductive and/or magnetizable solids, the particles having an average particle size in the range from 1 to 1000 nm.

15. The method according to claim 14, wherein the heating medium is selected from particles of magnetizable solids, each particle containing a core of a magnetizable material that is sheathed by a non-magnetic material.

* * * * *